United States Patent
Serban et al.

(10) Patent No.: US 8,230,720 B2
(45) Date of Patent: Jul. 31, 2012

(54) FUNCTIONALIZED MONOLAYERS FOR CARBON DIOXIDE DETECTION BY A RESONANT NANOSENSOR

(75) Inventors: Bogdan-Catalin Serban, Bucharest (RO); Cornel Cobianu, Bucharest (RO); Mihai N. Mihaila, Bucharest (RO); Viorel-Georgel Dumitru, Ploiesti (RO)

(73) Assignee: Honeywell International Inc., Morristown, NJ (US)

( * ) Notice: Subject to any disclaimer, the term of this patent is extended or adjusted under 35 U.S.C. 154(b) by 121 days.

(21) Appl. No.: 12/856,891

(22) Filed: Aug. 16, 2010

(65) Prior Publication Data
US 2011/0116974 A1    May 19, 2011

Related U.S. Application Data

(60) Provisional application No. 61/262,702, filed on Nov. 19, 2009.

(51) Int. Cl.
*G01N 29/02* (2006.01)
*G01N 7/00* (2006.01)
*G01N 21/00* (2006.01)
*G01N 27/00* (2006.01)
*G01N 31/00* (2006.01)
*G01N 33/00* (2006.01)
*G01N 30/96* (2006.01)

(52) U.S. Cl. .......... 73/24.01; 73/24.06; 422/83; 422/88; 422/98

(58) Field of Classification Search .................. 73/24.01; 422/88
See application file for complete search history.

(56) References Cited

U.S. PATENT DOCUMENTS

| 7,489,537 | B2 | 2/2009 | Tran |
| 7,914,740 | B2 * | 3/2011 | Zhang et al. ................ 422/68.1 |
| 2005/0003560 | A1 * | 1/2005 | Zeng et al. .................. 436/527 |
| 2007/0125181 | A1 | 6/2007 | Ofek et al. |
| 2007/0285843 | A1 | 12/2007 | Tran |

(Continued)

FOREIGN PATENT DOCUMENTS
EP        72744 A2 *  2/1983

OTHER PUBLICATIONS

Bergbreiter, A. et al., "fabrication, structure, and chemical properties of surface confined alloys," http://www.uni-ulm_de/~hhoster/personal/surface_alloys.html, Ulm University, Germany.

(Continued)

*Primary Examiner* — Jill Warden
*Assistant Examiner* — Charles D Hammond
(74) *Attorney, Agent, or Firm* — Kermit D. Lopez; Luis M. Ortiz; Melissa Asfahani

(57) ABSTRACT

A resonant nanosensor apparatus associated with a functionalized monolayer for detecting carbon dioxide and a method of forming the same. A wafer including a sensing vibrating beam and a reference vibrating beam may be functionalized with a functional group in order to form a sensing self monolayer. The sensing self assembled monolayer may be configured by bridging oxygen or carbon atoms covalently bonded with respect to the vibrating beams. A liquid solution of hydrochloric acid may then be applied to the sensing self assembled monolayer at the surface of the reference beam by a direct printing process to obtain a reference monolayer. The liquid solution of HCl transforms the functional groups responsible for the carbon dioxide detection into protonated groups, which do not react with carbon dioxide, but possess visco-elastic properties similar to that of the sensing monolayer.

16 Claims, 7 Drawing Sheets

U.S. PATENT DOCUMENTS

2008/0054382 A1    3/2008  Stetter
2008/0229831 A1*   9/2008  Serban et al. .................. 73/589
2010/0137731 A1    6/2010  Star et al.
2011/0113856 A1*   5/2011  Cobianu et al. .............. 73/24.06

OTHER PUBLICATIONS

Self-assembled monolayer—Wikipedia, http://en.wikipedia.org/wiki/Self-assembled_monolayer (2009).

* cited by examiner

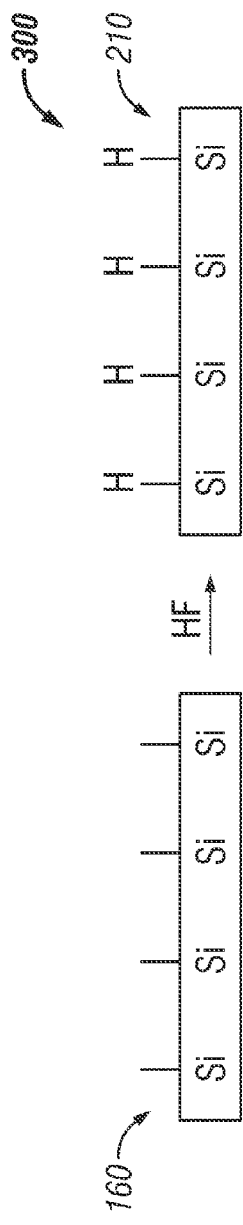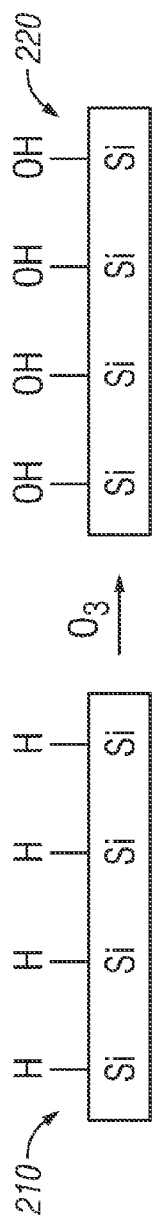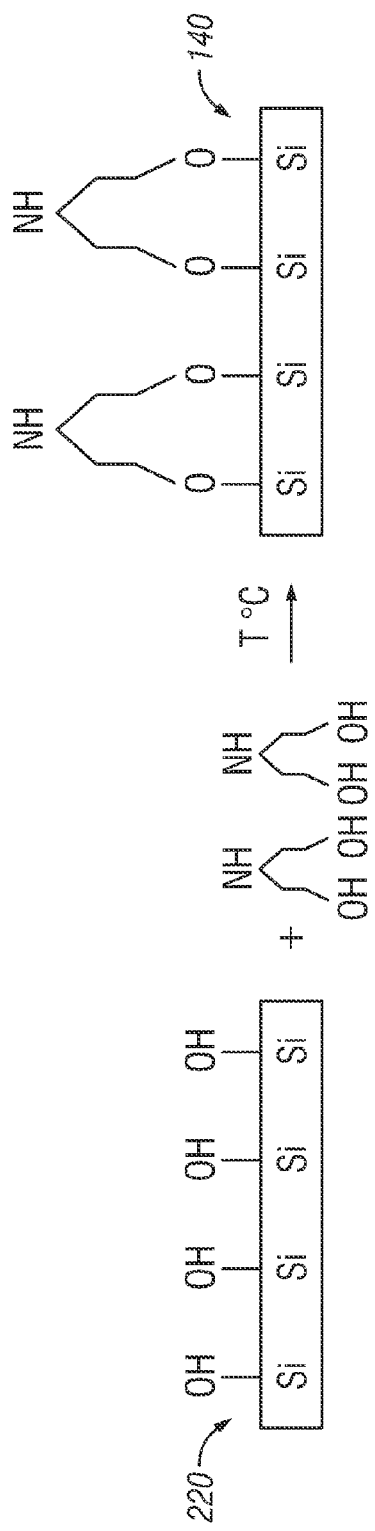

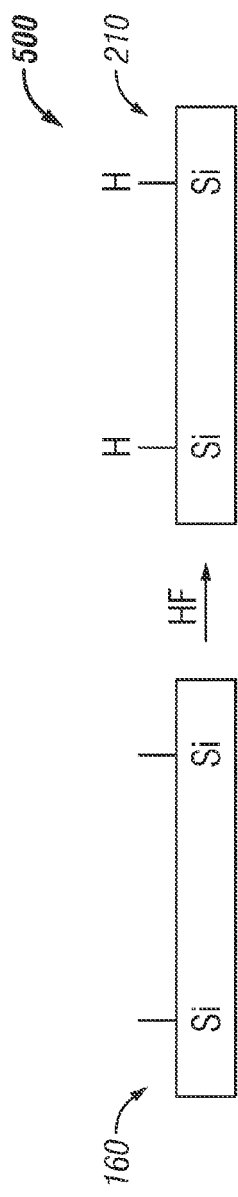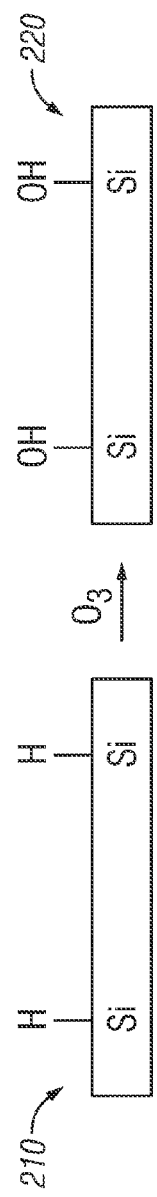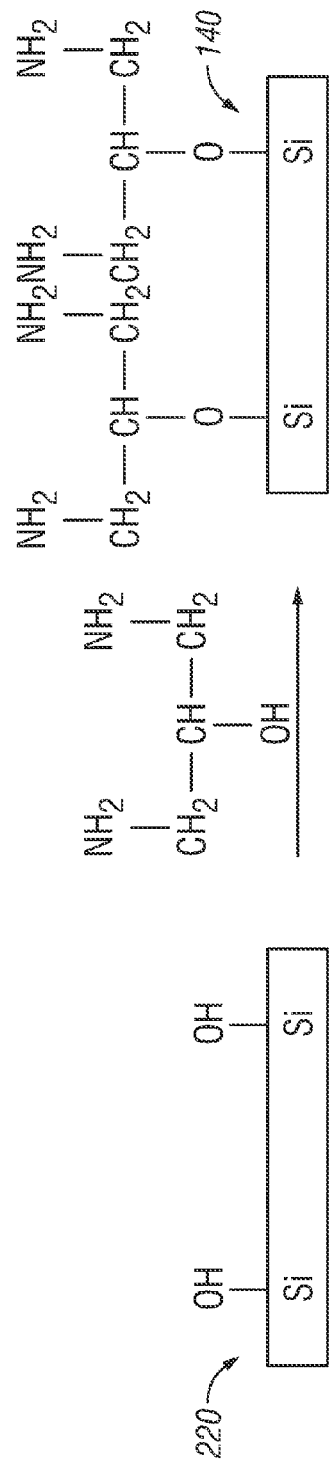
FIG. 13
FIG. 14
FIG. 15

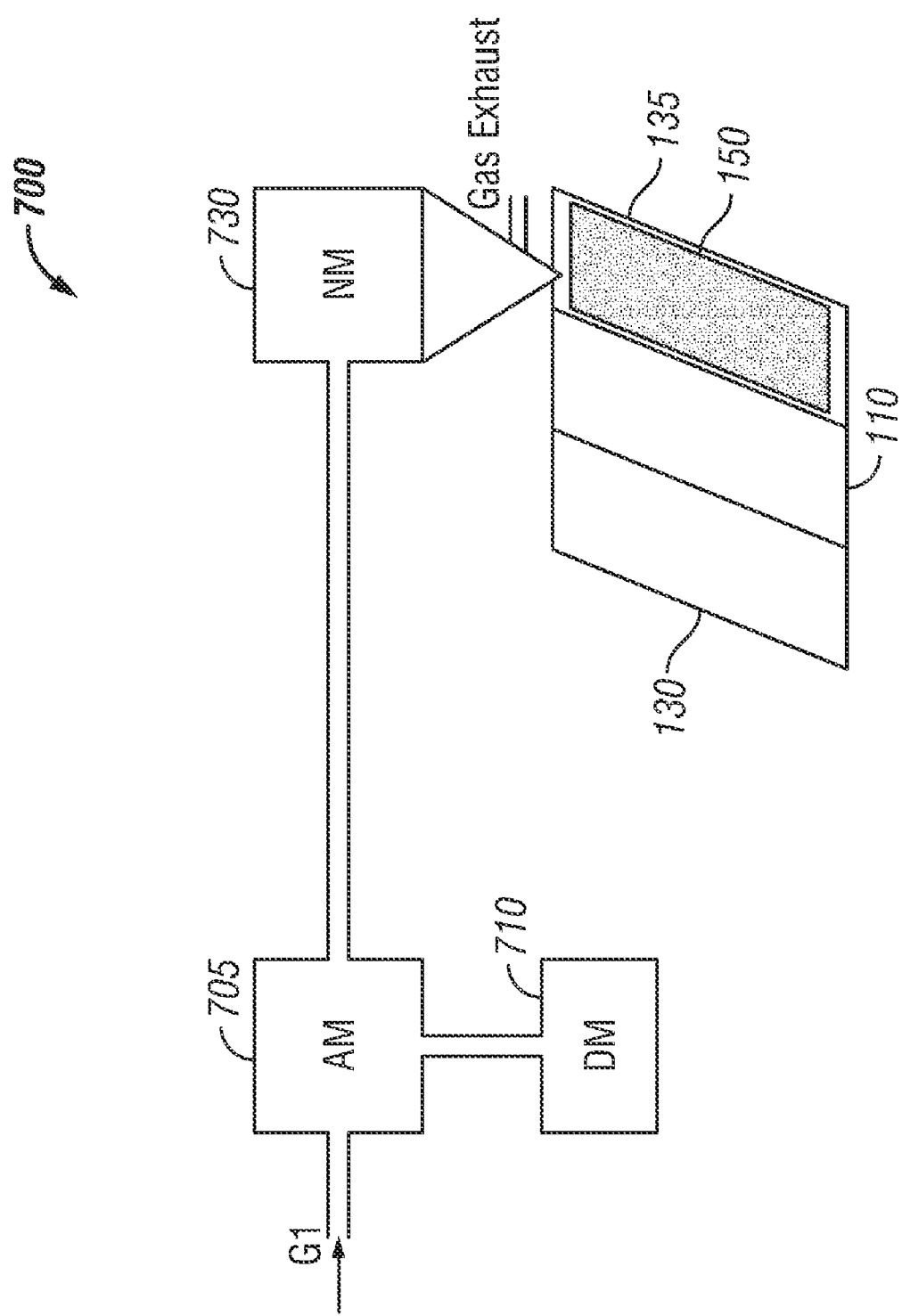

FUNCTIONALIZED MONOLAYERS FOR CARBON DIOXIDE DETECTION BY A RESONANT NANOSENSOR

CROSS-REFERENCE TO PROVISIONAL APPLICATION

This application claims priority under 35 U.S.C. §119(e) to U.S. Provisional Application Ser. No. 61/262,702, entitled "Functionalized Monolayers for Carbon Dioxide Detection by a Resonant Nanosensor," filed on Nov. 19, 2009, the entire disclosure of which is hereby incorporated by reference for all purposes as if fully set forth herein.

TECHNICAL FIELD

Embodiments are generally related to sensing devices and techniques. Embodiments are also related to nano-electromechanical systems (NEMS) for gas sensing applications. Embodiments are additionally related to functionalized monolayers and nano-resonators.

BACKGROUND OF THE INVENTION

As the demand for energy resources increases simultaneously with the decrease in available fossil fuels, various alternative sources of energy such as coal-based energy technologies, for example, are being deployed. Large amounts of $CO_2$ are generated by coal gasification processes in power plants, for example, which trigger a need for carbon capture and sequestration (CCS) as well as $CO_2$ monitoring over large areas to avoid ecologic disasters. The potential toxic gas emissions from such power plants have resulted in the need for $CO_2$ sensors capable of being fabricated in large volumes, while offering low cost/drift/electrical power consumption and a high sensitivity and selectivity when utilized to monitor $CO_2$ concentration in air. Additionally, such sensors in association with a wireless sensing network must be able to detect any deviation from the normal $CO_2$ environmental concentration, which is in the range of 380-440 ppm, depending on the specific region and season.

The majority of prior art $CO_2$ sensors are based on electrochemical and optical principles. Unfortunately, the cost for fabricating such sensors for large area $CO_2$ monitoring is high. One of the possible sensing solutions for $CO_2$ detection at low cost, low power consumption with high sensitivity and selectivity at low gas concentrations is the use of a resonant nano-electro-mechanical system (NEMS) sensor, which may also be referred to as a nanosensor.

The resonance frequency with respect to such a resonant nanosensor may be changed by selective $CO_2$ adsorption and reaction on a functionalized surface of a silicon beam, which mechanically vibrates at a frequency equal to the frequency of an excitation force. Problems associated with prior art resonant sensors, and which may propagate to emerging resonant nanosensor devices, include a lack of long term performance stability and a poor drift behavior due to poor baseline stability (i.e., recovery of the sensor signal to the same response level in the absence of the gas to be detected). Other problems include its inherent temperature variations and temperature dependence of the resonance frequency, the fatigue of the vibrating beam, humidity absorption, and aging of its sensing layer, which may exhibit or contribute to a baseline drift.

Based on the foregoing, it is believed that a need exists for an improved differential resonant nanosensor apparatus for detecting carbon dioxide. A need also exists for an improved method for forming functionalized monolayers on a vibrating nanobeam surface, as described in greater detail herein.

BRIEF SUMMARY

The following summary is provided to facilitate an understanding of some of the innovative features unique to the disclosed embodiments and is not intended to be a full description. A full appreciation of the various aspects of the embodiments disclosed herein can be gained by taking the entire specification, claims, drawings, and abstract as a whole.

It is, therefore, one aspect of the disclosed embodiment to provide for an improved resonant nanosensor apparatus and method.

It is another aspect of the disclosed embodiment to provide for a new method for forming functionalized monolayers on the surface of a vibrating nanobeam.

It is a further aspect of the disclosed embodiment to provide for a new method for forming a reference monolayer that does not react with carbon dioxide.

The aforementioned aspects and other objectives and advantages can now be achieved as described herein. A resonant nanosensor apparatus having functionalized monolayers for detecting carbon dioxide and a method of forming the same are disclosed. A wafer can be configured from, for example, one or more IC chips, wherein each chip includes a sensing vibrating beam and a reference vibrating beam (e.g., silicon) that may be selectively functionalized with functional groups (e.g., amino terminated group) in order to form a sensing monolayer. The sensing monolayer may be configured by bridging atoms (e.g., oxygen atoms, carbon atoms) with respect to the vibrating beams. A liquid solution of hydrochloric acid (HCl) may then be applied to the sensing monolayer at the surface of the reference beam to obtain a non-sensing reference monolayer. The liquid solution of HCl transforms the functional group responsible for the carbon dioxide detection into hydrochlorides, which do not react with carbon dioxide, but possess similar visco-elastic properties (e.g., temperature, humidity and aging) as the sensing monolayer.

The sensing monolayer can be configured by bridging the oxygen atoms with respect to the vibrating beam. The processed wafer comprising the vibrating beams and a metallization layer may be cleaned in a solution (e.g., isopropyl alcohol) and rinsed with de-ionized water. The wafer may then be immersed in diluted hydrofluoric acid and de-ionized water in order to generate a hydrogen terminated surface. The hydrogen terminated surface may be exposed to a flow of ozone in order to obtain a hydroxyl terminated surface. The hydroxyl terminated surface may be immersed in a sealed flask containing amino alcohol (e.g., 4 amino-1 butanol; 4-N-methyl amino-1-butanol; 5 amino 1-pentanol; 5 N-methyl amino-1 pentanol; 6 amino-1 hexanol; 6 methylamino-1 hexanol; ethanol amine; diethanolamine; and 1,3 diamino 2-propanol) and heated in dry nitrogen in order to form the sensing monolayer on the wafer by a poly-condensation reaction.

The sensing monolayer can also be configured by bridging the carbon atoms with respect to the vibrating beams. The wafer containing the hydrogen-terminated surface may be immersed in a sealed flask containing a mixture of unprotected amine (e.g., 3 butenyl-amine-Cbz; and N-methyl-3butenylamine-Cbz) and heated in toluene in order to form the sensing monolayer connected to the wafer surface by the carbon atoms. The reference monolayer containing only non-sensing protonated terminal groups may be obtained from the sensing monolayer by exposing the reference beam to liquid HCl by a direct printing process on the reference beam. The disclosed differential resonant nanosensor apparatus containing sensing and reference layers can therefore provide a genuine all-differential gas sensing application.

BRIEF DESCRIPTION OF THE DRAWINGS

The accompanying figures, in which like reference numerals refer to identical or functionally-similar elements throughout the separate views and which are incorporated in and form a part of the specification, further illustrate the disclosed embodiments and, together with the detailed description of the invention, serve to explain the principles of the present invention.

FIGS. 7-9 illustrate a sequence of chemical reactions for forming the sensing monolayer based on bridging oxygen atoms with respect to the silicon vibrating beam, in accordance with the disclosed embodiments;

FIGS. 13-15 illustrate a sequence of chemical reactions for forming the sensing monolayer based on bridging oxygen atoms with respect to the silicon vibrating beam, in accordance with the disclosed embodiments; and FIG. 16 illustrates a block diagram of a direct printing system, in accordance with the disclosed embodiments.

DETAILED DESCRIPTION

The particular values and configurations discussed in these non-limiting examples can be varied and are cited merely to illustrate one or more embodiments and are not intended to limit the scope thereof.

Figure 1:
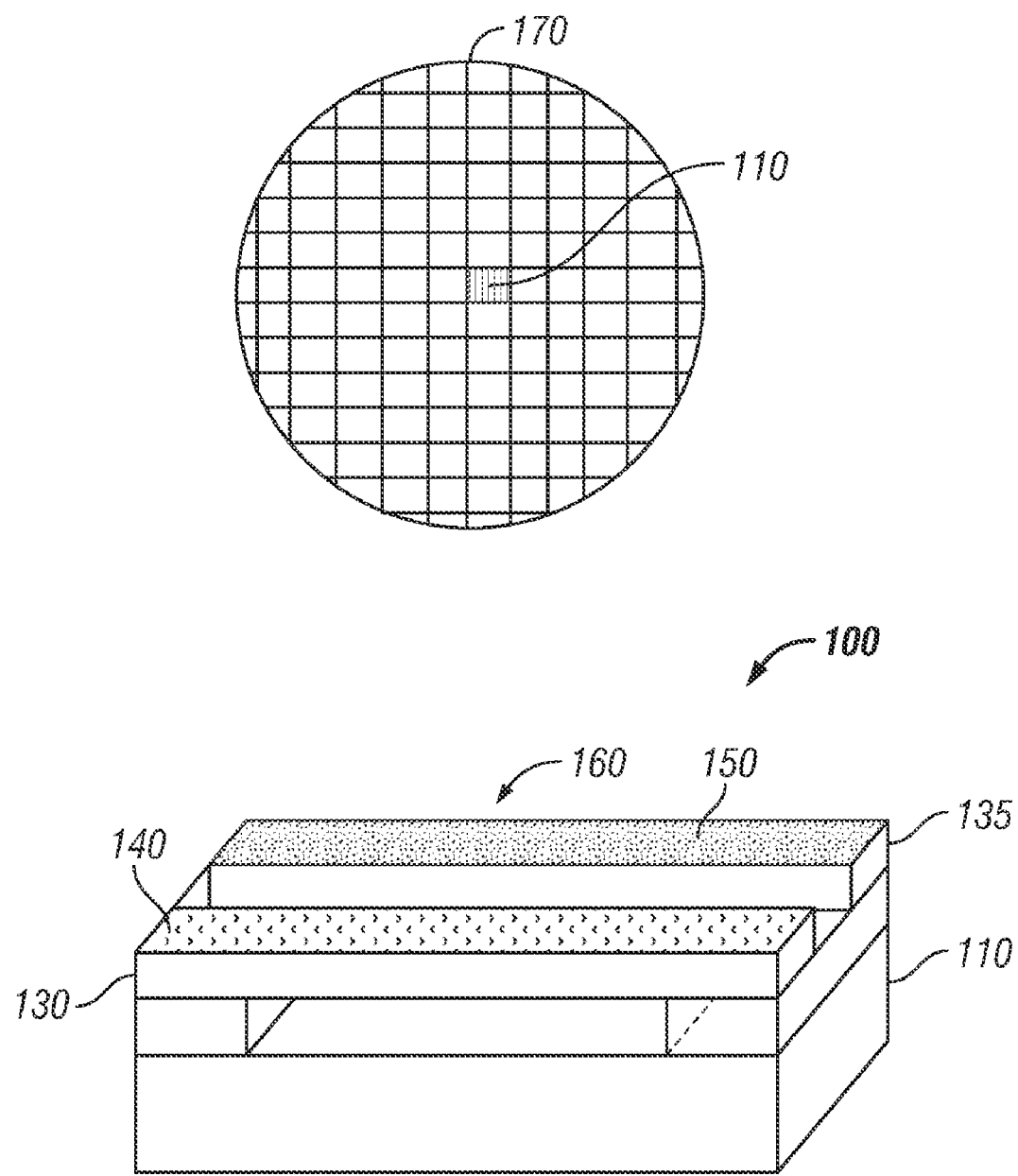
FIG. 1 illustrates a perspective view of a resonant nanosensor apparatus and a top view of a wafer containing a plurality of nanosensors, in accordance with the disclosed embodiments.

FIG. 1 illustrates a perspective view of an exemplary resonant nanosensor apparatus 100 and a schematic view of a processed silicon wafer containing a multitude of resonant nanosensor(s) 100, in accordance with the disclosed embodiments. Note that in FIGS. 1-16, identical or similar blocks are generally indicated by identical reference numerals. The resonant nanosensor apparatus 100 with gas detection capability may be employed to detect a gas (e.g. carbon dioxide) by eliminating base line drift issues. The apparatus 100 generally includes a sensing resonant beam 130 and a reference resonant beam 135 located on a chip 110, included in the wafer 170, which contains a multitude of such chips 110. The sensing beam 130 further includes a sensing monolayer 140 and the reference beam 135 includes a reference self assembled monolayer 150. The wafer 170, the chip 110, and its associated sensing resonant beam 130 and the reference resonant beam 135 may be configured from a material such as, for example, silicon, depending upon design considerations. It can be appreciated that other types of materials may be utilized in place of the suggested material.

The sensing monolayer 140 and the reference monolayer 150 comprises an organized layer of molecules in which one end of the molecule, the "head group", shows a specific covalent bond with respect to the beam 130 and 135, where either oxygen or carbon atoms are used as bridges between the monolayer and the surface of the resonant beam. The sensing monolayer 140 may be employed to sense ultra small concentration of gases loading on the beam 130 and which may thus change the resonance mechanical frequency of the vibrating beam as a function of the amount of that gas selectively and reversibly reacting with that sensing monolayer 140. Unfortunately, the resonance frequency shift of the functionalized sensing resonant beam 130 may include not only data regarding the gas to be detected, but as well as the effects of temperature, humidity variations, gas atoms adsorption-desorption fluctuations on the electro-mechanical behavior of resonator beam 130, and finally the effects of aging of the sensing self assembled monolayer 140. Similarly, the resonance frequency shift of the reference resonant beam 135 may include data regarding temperature, humidity variations, atom adsorption-desorption fluctuations on the resonator 135, and the aging of the reference monolayer 150.

The resonance frequency signal from the sensing resonant beam 130 may be mixed with the resonance frequency signal from the reference resonant beam 135, in order to provide a drift-free signal of frequency carrying only information regarding the gas to be detected. The common mode signal of the sensing and the reference resonators 130 and 135 due to temperature variation, humidity adsorption, aging of the resonators 130 and 135 may be rejected by means of an-all differential approach with respect to the sensor as disclosed herein.

Figure 2:
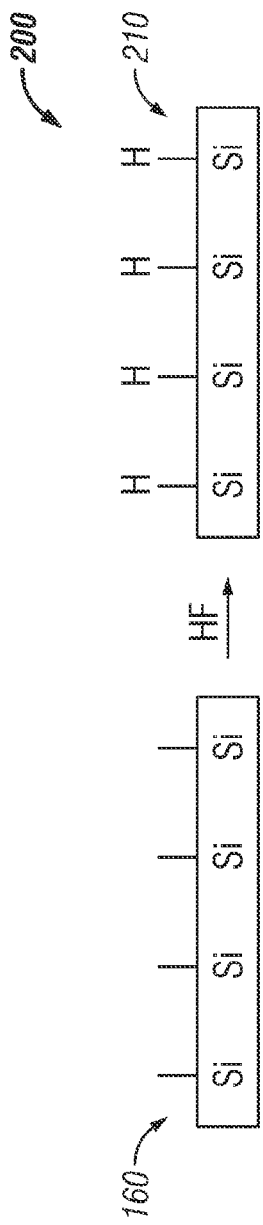
FIGS. 2-4 illustrate a sequence of chemical reactions for forming a sensing monolayer based on bridging oxygen atoms with respect to a silicon vibrating beam, in accordance with the disclosed embodiments.
Figure 3:
Figure 4:
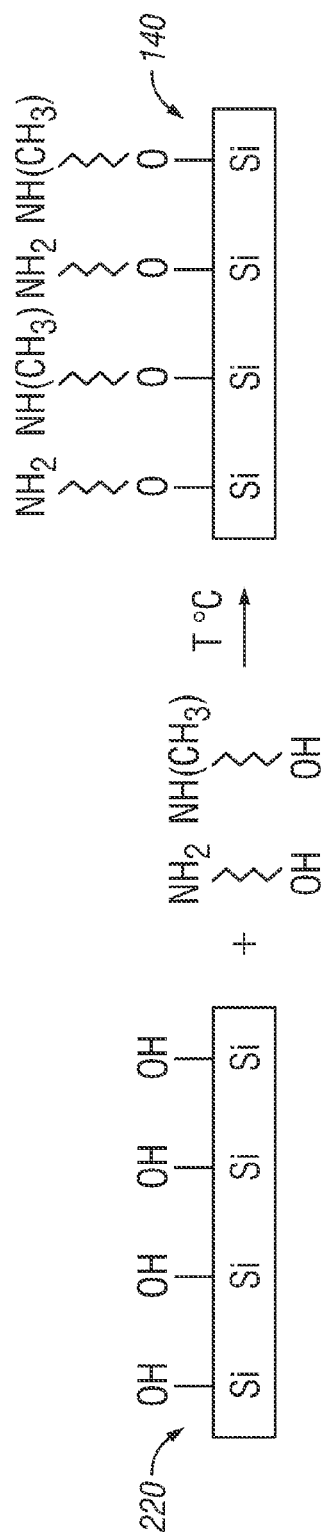

FIGS. 2-4 illustrate a sequence of chemical reactions 200 for forming the sensing monolayer 140 based on bridging oxygen atoms with respect to the silicon vibrating beams surface 160, comprising both the sensing 130 and reference beam 135 surfaces at this stage, in accordance with the disclosed embodiments. The monolayers employed in the disclosed embodiments are produced from molecules or blocks that include at least two functional groups, i.e., a first functional group capable of being attached to a surface, and a second functional group which is capable of being covalently bonded with the first functional group. The use of blocks having such a combination of functional groups allows for the sequential buildup of monolayers on a surface. The sensing monolayer 140 may be formed by bridging the oxygen atoms with respect to the vibrating beams 160 by means of polycondensation reaction between different amino alcohols and hydroxyl groups on the silicon vibrating beam surface 160.

The processed silicon wafer 170 can be configured from a multitude of chips 110, wherein each contains suspended silicon nanobeam 130 and 135 and metallization layer (e.g., AuCr) may be cleaned for 1 hour in isopropyl alcohol and rinsed with de-ionized water. The wafer 170 may then be immersed in 2% hydrofluoric acid (HF) and de-ionized water (DI) for five minutes in order to etch away the native $SiO_2$ on the Si surfaces 160 of the wafer 170 and generate Si—H bonds 210 on all the Si surfaces 160, as illustrated in FIG. 2. The wafer 170 having the chip containing the surface samples 210 may be exposed to a flow of ozone ($O_3$) for 25 minutes in order to obtain hydroxyl (OH) terminated silicon surfaces 220, as shown in FIG. 3.

The wafer 170 containing the chips 110 and the OH terminated silicon surfaces 220 (still comprising the surfaces of both sensing beam 130 and reference beam 135, at this stage)

may then be immersed in a sealed flask containing amino alcohols heated at 150° C. for four hours in dry nitrogen in order to form the $CO_2$ sensing monolayer 140 on the Si surfaces 160 by poly-condensation reaction. The amino alcohols may be selected from the group consisting of 4 amino-1 butanol, 4-N-methyl amino-1-butanol, 5 amino 1-pentanol, 5 N-methyl amino-1 pentanol, 6 amino-1 hexanol, 6 methylamino-1 hexanol, ethanol amine, diethanolamine, 1,3 diamino 2-propanol. FIG. 4 illustrates a poly-condensation reaction between the OH terminated Si surface 220 and 4 amino-1 butanol in order to form the $CO_2$ sensing monolayer 140.

Figure 5:
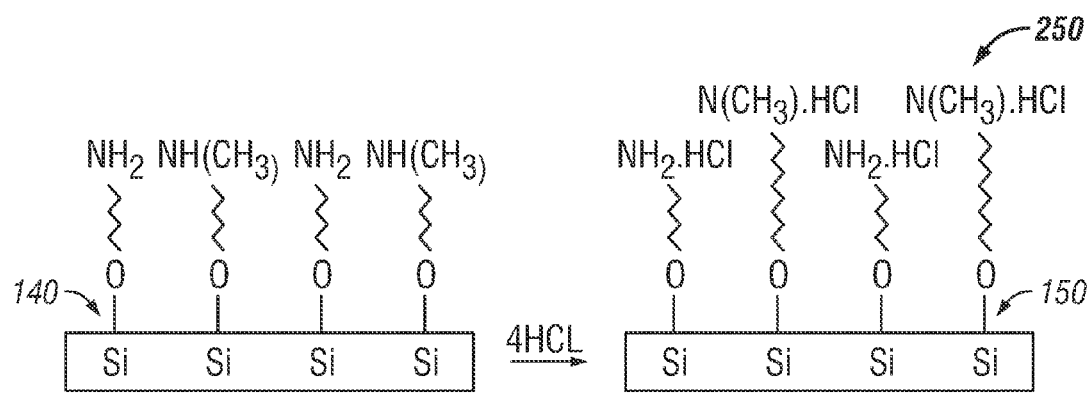
FIG. 5 illustrates a chemical reaction for forming a reference monolayer by exposing a reference-vibrating beam to liquid HCl, in accordance with the disclosed embodiments.
Figure 6:
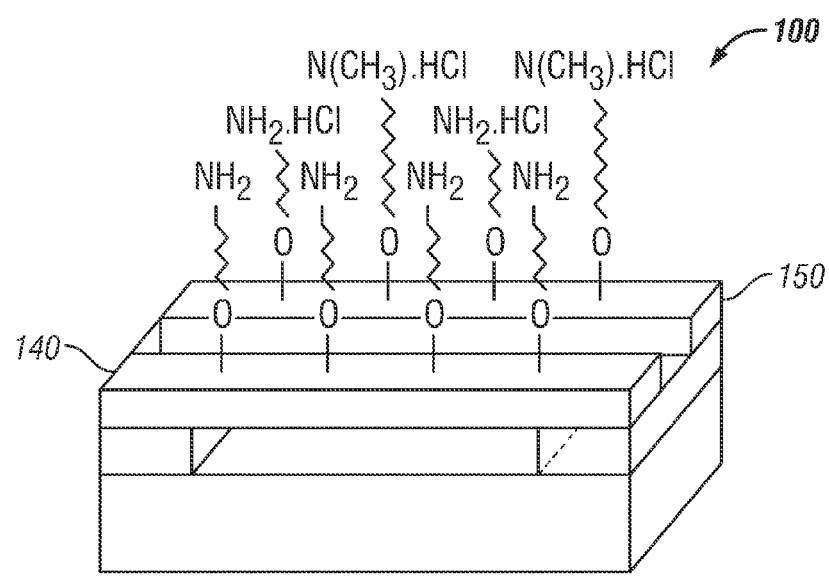
FIG. 6 illustrates a schematic view of the all-resonant nanosensor apparatus associated with sensing and reference monolayer, in accordance with the disclosed embodiments.

FIG. 5 illustrates a final chemical reaction 250 for forming the reference monolayer 150, only on the reference beam 135 of all the chips 110 contained in the wafer 170. This "reference" functionalization reaction is obtained by exposing only the reference vibrating beams 135 comprising also the $CO_2$ sensing monolayer 140 to liquid HCl, in accordance with the disclosed embodiments. A liquid solution of HCl may be applied on the sensing monolayer 140 at the surface of the reference beam 135 by a direct printing approach 700 to obtain the reference monolayer 150. The liquid solution of HCl transforms all the amino groups responsible for the $CO_2$ detection into protonated terminal groups, which does not react with $CO_2$, and thus it obtains a reference monolayer 150, which possesses similar visco-elastic properties (e.g., temperature, humidity and aging) as the sensing monolayer 140, but no sensing properties. FIG. 6 illustrates a schematic view of the resonant nanosensor apparatus 100 associated with sensing and reference monolayer 140 and 150, in accordance with the disclosed embodiments.

FIGS. 7-9 illustrate a sequence of chemical reactions 300 for forming another type of sensing monolayer 140 based on bridging oxygen atoms with respect to the silicon vibrating beam surface 160, in accordance with the disclosed embodiments, and where for each two bridging oxygen atoms, we obtain a NH sensing termination of the monolayer 140. FIG. 9 illustrates the poly-condensation reaction between the OH terminated Si surface 220 and di-ethanolamine and ethanolamine in order to form the $CO_2$ sensing monolayer 140, on both the sensing beam 130 and the reference beam 135, at this stage of the reaction sequence. After formation of the sensing monolayer 140, the samples may be rinsed with isopropyl alcohol, DI water, and dried in $N_2$ stream. The amino groups associated with the amino alcohols diethanolamine, 1,3 diamino 2-propanol, which are responsible for carbon dioxide detection, possess two oxygen-terminated anchors onto the silicon surface 220, for each amino group. This may provide increased stability of the monolayer 140 due to its stronger bonding on the surface. A mixture of primary amines/secondary amines may be employed as sensing monolayer for carbon dioxide detection. For this functionalization route, the reference monolayer 150 can be obtained in a similar manner as described above, wherein the amino groups from the reference beams 135 react with the liquid HCl deposited selectively by a direct printing process 700 only on the reference nanobeam 135 in order to obtain hydrochlorides which do not react with $CO_2$.

Figure 10:
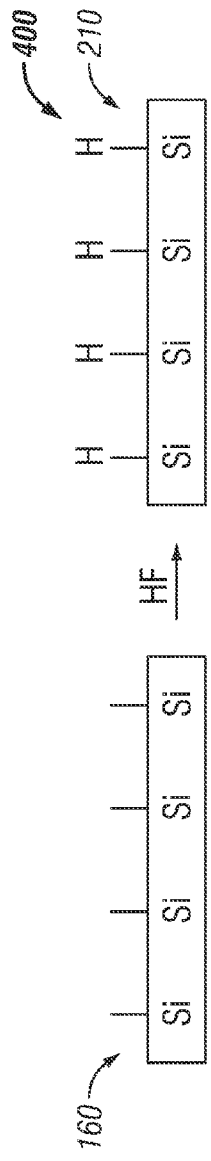
FIGS. 10-12 illustrate a sequence of chemical reactions for forming the sensing monolayer based on bridging carbon atoms with respect to the silicon vibrating beam, in accordance with the disclosed embodiments.
Figure 11:
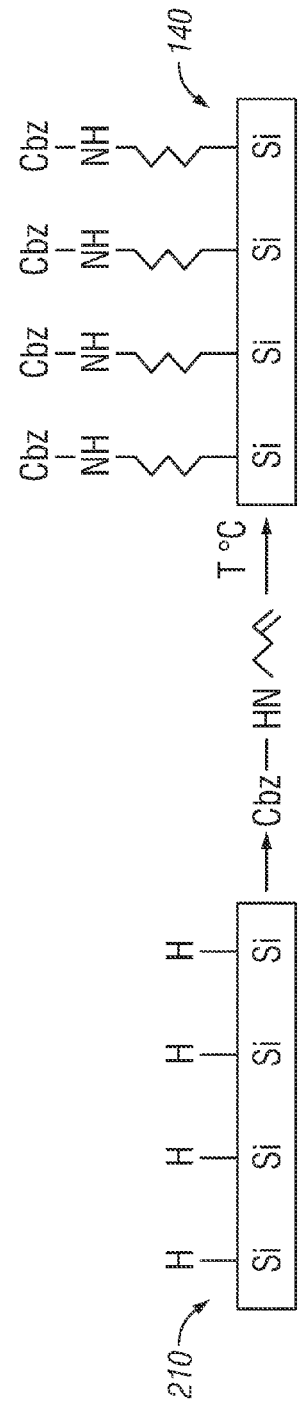
Figure 12:
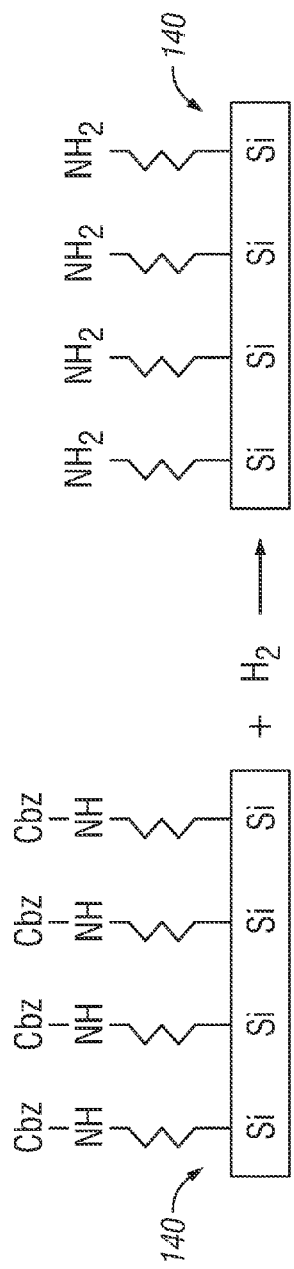

FIGS. 10-12 illustrate a sequence of chemical reactions 400 for forming the sensing monolayer 140 based on bridging carbon atoms covalently bonded with respect to the silicon vibrating beam surfaces 160, in accordance with the disclosed embodiments. The processed silicon wafer 170 made of the chips 110, which are containing suspended silicon nanobeam 130 and 135 and metallization layer (e.g., AuCr) may be cleaned for 1 hour in isopropyl alcohol and rinsed with de-ionized water. The wafer 170 may then be immersed in 2% hydrofluoric acid (HF) in de-ionized water (DI) for five minutes in order to etch away the native $SiO_2$ layer on the Si surfaces 160 and generate Si—H bonds 210 on the Si surface 160, as illustrated in FIG. 10.

The wafers 170 with the hydrogen terminated Si surface 210 may be immersed in a sealed flask containing 3-butenylamine-Cbz and the vessel may be heated in toluene at 150° C. for four hours for forming the monolayer 140 connected to the Si surface 160 by carbon atoms, as shown in FIG. 11. The mixture of the reaction may be cooled to room temperature and the functionalized silicon surface 160 may be rinsed with ethanol and de-ionized water. The de-protection of the amino group through hydrogenation is illustrated in FIG. 12. The reference monolayer 150 containing only non-sensing protonated terminal groups may be obtained from the sensing monolayer 140 by exposing only the reference beam 135 to liquid HCl, by means of the direct printing process 700 on the reference beam 135.

FIGS. 13-15 illustrate a sequence of chemical reactions 500 for forming another type of sensing monolayer 140 based on bridging oxygen atoms with respect to the silicon vibrating beam 160, in accordance with the disclosed embodiments, wherein for each oxygen bridging atom two $NH_2$ sensing terminations are obtained on the monolayer 140. As indicated in FIG. 15, for this chemical route, the sensing monolayer 140 is obtained by the polycondensation reaction between the hydroxyl-terminated silicon surfaces 220 and 1,3 di-amino 2 propanol. As can be seen in all these chemical synthesis, the sensing monolayer 140 comprises an organized layer of molecules, which includes a terminal group, which may be covalently attached to the silicon beam surface 160 and the other which may be functionalized for gas recognition and detection. The selection of sensitive terminal groups, which may be incorporated in the monolayers, can be based on the hard soft acid base (HSAB) rule. According to such theory, a hard Lewis base prefers to bond to a hard Lewis acid and a soft Lewis base prefer to bond to a soft Lewis acid. $CO_2$ is a hard acid and, according to HSAB rule, it can interact with the amino groups, which are hard bases. Such interaction is an acid-base equilibrium, which is reversible and may lead to the formation of carbonates.

FIG. 16 illustrates a block diagram of a direct printing system 700 for preparing the functional reference monolayer 150 associated with the all-differential resonant nanosensor apparatus 100 on the reference beam 135, in accordance with the disclosed embodiments. The reference monolayer 150 may be obtained from the sensing monolayer 140 by exposing the reference beam 135 to liquid HCl by using the additive, selective direct printing system 700. The direct printing system 700 generally constitutes a distribution system for local, selective, and additive deposition of the liquid phase of the particular material. FIG. 16 depicts the printing process only at the chip level 110, but it can be appreciated that this printing process can be repeated for any chip 110 of the wafer 170 in essentially a step and repeat process.

The homogeneous liquid phase of HCl solution is prepared in a first stage. The wafer 170 can be brought immediately from the previous technological process to this direct printing process so there is no need for a further cleaning before this process. Before starting any deposition process, the nozzle head is positioned at the appropriate location on the chip 110 as per lay-out computer program of the wafer 170. Then, an input gas G1 can be passed through an atomizer module AM 705. The input gas G1 is further processed by a deposition material module DM 710 to generate an atomized liquid solution of HCl. By the step and repeat process, the atomized liquid solution of HCl may be employed to generate multiple reference layers on all reference beams 135 of the chips 110 from wafer 170 through a nozzle module NM 730 by additive deposition of the HCl solution in the right place on each chip 110. Thereafter, the transition of the nanobeam 135 from $CO_2$ sensing capability to no sensing capabilities is obtained by the amino group reaction of sensing SAM with the HCl molecules in order to obtain non-sensing protonated terminal groups, as described herein.

The all-differential NEMS resonant nanosensor disclosed herein offers a number of advantages, including solving baseline drift issues with respect to differential sensing and measurement principles. The ambient humidity and temperature variations, as well as all the effect of aging, fatigue with respect to the beam 130 and circuits (including a major contribution from phase noise in electronic oscillators) may provide a common mode signal that is rejected from the "all differential" sensing process.

Based on the foregoing, it can be appreciated that in one embodiment a method is disclosed for forming a functionalized monolayer for $CO_2$ sensing. Such a method can include: configuring a sensing monolayer functionalized with at least one functional group on a surface of a sensing vibrating beam and a reference vibrating beam located on a wafer in order to detect a presence of carbon dioxide gas, and applying a solution of hydrochloric acid to the sensing monolayer formed at the surface of the reference vibrating beam to form a reference monolayer with a non-sensing protonated terminal group, wherein the reference monolayer includes visco-elastic properties similar to that of the sensing monolayer, but lacking sensing properties.

In another embodiment, such a method can include forming the sensing monolayer by bridging oxygen atoms covalently bonded with respect to the sensing vibrating beam and the reference vibrating beam. Additionally, in another embodiment, such a method can include forming the sensing monolayer by bridge carbon atoms covalently bonded with respect to the sensing vibrating beam and the reference vibrating beam. In a further embodiment, such a method can include depositing the solution of hydrochloric acid on the sensing monolayer of the reference vibrating beam by direct printing in order to obtain a reference monolayer with similar visco-elastic properties and no sensing properties. Additionally, in some embodiments, the wafer can be configured as silicon or another appropriate material.

Additionally, in alternative embodiments, such a method can include: cleaning the wafer comprising the vibrating beams and a metallization layer in isopropyl alcohol in order to thereby rinse with de-ionized water; and immersing the wafer in diluted hydrofluoric acid and de-ionized water in order to generate a hydrogen terminated surface. In other embodiments, forming the sensing monolayer by bridging oxygen atoms can include: exposing said hydrogen terminated surface to a flow of ozone in order to obtain a hydroxyl terminated surface, and immersing said hydroxyl terminated surface in a sealed flask containing amino alcohol and heating in dry nitrogen in order to form said sensing monolayer on said wafer by a poly-condensation reaction and getting a sensing amino terminal group for each bridging oxygen atom.

Additionally, in some embodiments of such a method, the amino alcohol discussed herein can be selected from a functional group comprising one or more of the following: 4 amino-1 butanol; 4-N-methyl amino-1-butanol; 5 amino 1-pentanol; 5 N-methyl amino-1 pentanol; 6 amino-1 hexanol; 6 methylamino-1 hexanol; ethanol amine; diethanolamine; and 1,3 diamino 2-propanol.

In further varying embodiments of such a method, forming the sensing monolayer by bridging carbon atoms can involve immersing the hydrogen terminated surface in a sealed container including a mixture of unprotected amine and heating the hydrogen terminated surface in toluene in order to form the sensing monolayer connected to the wafer by the bridging carbon atoms with one amino group obtained for each bridging carbon atom. In other embodiments, the unprotected amine can be selected from a functional group comprising, for example, at least one of the following: 3 butenyl-amine-Cbz and N-methyl-3butenylamine-Cbz.

It can be further appreciated that in another embodiment, a functionalized monolayer all-differential system for $CO_2$ sensing is disclosed, which includes: a sensing vibrating beam and a reference vibrating beam located on a wafer, a sensing monolayer functionalized with at least one functional group on the surface of the sensing vibrating beam and the reference vibrating beam located on the wafer in order to detect a presence of carbon dioxide gas, and a solution of hydrochloric acid applied to the sensing monolayer formed at the surface of the reference vibrating beam to form a reference monolayer with a non-sensing protonated terminal group, wherein the reference monolayer includes visco-elastic properties similar to that of the sensing monolayer, but lacking the sensing properties.

In another embodiment of such a system, the sensing monolayer can be configured by bridging oxygen atoms with respect to the sensing vibrating beam and the reference vibrating beam. In still another embodiment of such a system, the sensing monolayer can be configured by bridging carbon atoms with respect to the sensing vibrating beam and the reference vibrating beam. In other embodiments of such a system, the aforementioned solution of hydrochloric acid can be deposited on the sensing monolayer of the reference vibrating beam by direct printing in order to obtain a reference monolayer with no sensing properties and similar visco-elastic properties.

In such a system, the wafer comprising the vibrating beams and a metallization layer can be cleaned in isopropyl alcohol and thereafter rinsed with de-ionized water. The wafer can also be immersed in diluted hydrofluoric acid and de-ionized water in order to generate a hydrogen terminated surface. The hydrogen terminated surface can be exposed to a flow of ozone in order to obtain a hydroxyl terminated surface and the hydroxyl terminated surface can be immersed in a sealed flask containing amino alcohol and heating in dry nitrogen in order to form the sensing monolayer on the wafer by a poly-condensation reaction and getting a sensing amino terminal group for each bridging oxygen atoms.

In an embodiment of such a system, the amino alcohol can be selected from a functional group comprising at least one of the following: 4 amino-1 butanol; 4-N-methyl amino-1-butanol; 5 amino 1-pentanol; 5 N-methyl amino-1 pentanol; 6 amino-1 hexanol; 6.methylamino-1 hexanol; ethanol amine; diethanolamine; and 1,3 diamino 2-propanol.

In another embodiment of such a system, the hydrogen terminated surface can be immersed in a sealed container including a mixture of unprotected amine and the hydrogen terminated surface can be heated in toluene in order to form the sensing monolayer connected to the wafer by the carbon atoms. The aforementioned unprotected amine, in some embodiments, can be selected from a functional group comprising at least one of the following: 3 butenyl-amine-Cbz; and N-methyl-3butenylamine-Cbz.

In another embodiment, a functionalized monolayer all-differential system for $CO_2$ sensing can be implemented. Such a system can include: a sensing vibrating beam and a reference vibrating beam located on a silicon wafer, and a sensing monolayer functionalized with at least one functional group on a surface of the sensing vibrating beam and the reference vibrating beam located on the silicon wafer in order to detect a presence of carbon dioxide gas. Additionally, in such a system, a solution of hydrochloric acid can be applied to the sensing monolayer formed at the surface of the reference vibrating beam to form a reference monolayer with a non-sensing protonated terminal group, wherein the reference monolayer includes visco-elastic properties similar to that of the sensing self assembled monolayer.

It will be appreciated that variations of the above-disclosed and other features and functions, or alternatives thereof may be desirably combined into many other different systems or applications. Also, that various presently unforeseen or unanticipated alternatives, modifications, variations or improvements therein may be subsequently made by those skilled in which are also intended to be encompassed by the following claims.

What is claimed is:

1. A method for forming a functionalized monolayer for $CO_2$ sensing, comprising:
    configuring a sensing monolayer functionalized with at least one functional group on a surface of a sensing vibrating beam and a reference vibrating beam located on a wafer to detect a presence of carbon dioxide gas; and
    applying a solution of hydrochloric acid to said sensing monolayer formed at said surface of said reference vibrating beam to form a reference monolayer with a non-sensing protonated terminal group, wherein said reference monolayer includes visco-elastic properties of said sensing monolayer, but lacking sensing properties.

2. The method of claim 1 further comprising forming said sensing monolayer by bridging oxygen atoms covalently bonded with respect to said sensing vibrating beam and said reference vibrating beam.

3. The method of claim 1 further comprising forming said sensing monolayer by bridging carbon atoms covalently bonded with respect to said sensing vibrating beam and said reference vibrating beam.

4. The method of claim 1 further comprising depositing said solution of hydrochloric acid on said sensing monolayer of said reference vibrating beam by direct printing.

5. The method of claim 1 wherein said wafer comprises silicon.

6. The method of claim 1 further comprising:
    cleaning said wafer comprising said vibrating beams and a metallization layer in isopropyl alcohol to thereby rinse with de-ionized water; and
    immersing said wafer in diluted hydrofluoric acid and de-ionized water to generate a hydrogen terminated surface.

7. The method of claim 2 wherein forming said sensing monolayer by bridging oxygen atoms, further comprises:
    exposing said hydrogen terminated surface to a flow of ozone to obtain a hydroxyl terminated surface; and
    immersing said hydroxyl terminated surface in a sealed flask containing amino alcohol and heating in dry nitrogen to form said sensing monolayer on said wafer by a poly-condensation reaction and getting a sensing amino terminal group for each said bridging oxygen atom.

8. The method of claim 7 wherein said amino alcohol is selected from a functional group comprising at least one of the following:
    4 amino-1 butanol;
    4-N-methyl amino-1-butanol;
    5 amino 1-pentanol;
    5 N-methyl amino-1 pentanol;
    6 amino-1 hexanol;
    6 methylamino-1 hexanol;
    ethanol amine;
    diethanolamine; and
    1,3 diamino 2-propanol.

9. The method of claim 3 wherein forming said sensing monolayer by bridging carbon atoms, further comprises:
    immersing a hydrogen terminated surface in a sealed container including a mixture of unprotected amine; and
    heating a hydrogen terminated surface in toluene in order to form said sensing monolayer connected to said wafer by said bridging carbon atoms with one amino group obtained for each said bridging carbon atom.

10. The method of claim 9 wherein said unprotected amine is selected from a functional group comprising at least one of the following:
    3 butenyl-amine-Cbz; and
    N-methyl-3butenylamine-Cbz.

11. A functionalized monolayer all-differential system for $CO_2$ sensing, said system comprising:
    a sensing vibrating beam and a reference vibrating beam located on a wafer;
    a sensing monolayer functionalized with at least one functional group on a surface of said sensing vibrating beam and said reference vibrating beam located on said wafer to detect a presence of carbon dioxide gas; and
    a solution of hydrochloric acid applied to said sensing monolayer formed at said surface of said reference vibrating beam to form a reference monolayer with a non-sensing protonated terminal group, wherein said reference monolayer includes visco-elastic properties of said sensing monolayer, but lacking the sensing properties.

12. The system of claim 11 wherein said sensing monolayer is configured by bridging oxygen atoms with respect to said sensing vibrating beam and said reference vibrating beam.

13. The system of claim 11 wherein said sensing monolayer is configured by bridging carbon atoms with respect to said sensing vibrating beam and said reference vibrating beam.

14. A functionalized monolayer all-differential system for $CO_2$ sensing, said system comprising:
    a sensing vibrating beam and a reference vibrating beam located on a silicon wafer;
    a sensing monolayer functionalized with at least one functional group on a surface of said sensing vibrating beam and said reference vibrating beam located on said silicon wafer to detect a presence of carbon dioxide gas; and
    a solution of hydrochloric acid applied to said sensing monolayer formed at said surface of said reference vibrating beam to form a reference monolayer with a non-sensing hydrochloride terminal group, wherein said reference monolayer includes visco-elastic properties that of said sensing monolayer.

15. The system of claim 14 wherein said sensing monolayer is configured by bridging oxygen atoms with respected to said sensing vibrating beam and said reference vibrating beam, wherein a hydrogen terminated surface is exposed to a flow of ozone to obtain a hydroxyl terminated surface; and said hydroxyl terminated surface is immersed in a sealed flask containing amino alcohol, wherein said hydroxyl terminated surface is heated in dry nitrogen to form said sensing monolayer on said wafer by a poly-condensation reaction and getting a sensing amino terminal group for each said bridging oxygen atom.

16. The system of claim 14 wherein said sensing monolayer is configured by bridging carbon atoms with respect to said sensing vibrating beam and said reference vibrating beam.

* * * * *